(12) United States Patent
Hsu et al.

(10) Patent No.: US 8,785,696 B2
(45) Date of Patent: Jul. 22, 2014

(54) PHOSPHORUS COMPOUND AND METHOD FOR PREPARING THE SAME

(75) Inventors: I-Cheng Hsu, Taipei (TW); Ping-Chieh Wang, Taipei (TW); An-Pang Tu, Taipei (TW); Kuen-Yuan Hwang, Taipei (TW)

(73) Assignee: ChangChun Plastics Co., Ltd., Taipei (TW)

( * ) Notice: Subject to any disclaimer, the term of this patent is extended or adjusted under 35 U.S.C. 154(b) by 439 days.

(21) Appl. No.: 12/611,591

(22) Filed: Nov. 3, 2009

(65) Prior Publication Data

US 2010/0125154 A1    May 20, 2010

(30) Foreign Application Priority Data

Nov. 14, 2008   (TW) ................................ 97144014 A

(51) Int. Cl.
  *C07F 9/02*   (2006.01)
  *C07F 9/28*   (2006.01)
  *C09K 21/12*  (2006.01)

(52) U.S. Cl.
  USPC ............................... 568/12; 562/19; 252/601

(58) Field of Classification Search
  USPC ............................... 568/12; 562/19; 252/601
  See application file for complete search history.

(56) References Cited

U.S. PATENT DOCUMENTS

| | | | | |
|---|---|---|---|---|
| 6,291,626 B1* | 9/2001 | Wang et al. | ..................... | 528/99 |
| 6,391,967 B1* | 5/2002 | Hwang et al. | ................. | 525/133 |
| 6,432,539 B1* | 8/2002 | Hwang et al. | ................. | 428/413 |
| 6,576,690 B1* | 6/2003 | Hwang et al. | ................. | 523/466 |
| 6,613,848 B1* | 9/2003 | Wang et al. | ..................... | 525/481 |
| 6,617,028 B1* | 9/2003 | Hwang et al. | ................. | 428/413 |
| 6,645,630 B1* | 11/2003 | Nakamura et al. | ............ | 428/413 |
| 6,646,064 B2* | 11/2003 | Wang et al. | ..................... | 525/523 |
| 6,720,077 B2* | 4/2004 | Hirai et al. | ..................... | 428/416 |
| 6,900,269 B2* | 5/2005 | Hwang et al. | ................. | 525/109 |
| 6,984,716 B2* | 1/2006 | Hwang et al. | ................. | 528/398 |
| 7,064,157 B2* | 6/2006 | Hwang et al. | ................. | 523/435 |
| 7,084,194 B2* | 8/2006 | Hwang et al. | ................. | 523/435 |
| 7,109,286 B2* | 9/2006 | Tamura et al. | ................ | 528/99 |
| 7,446,160 B2* | 11/2008 | Wang et al. | ..................... | 528/167 |
| 7,994,358 B2* | 8/2011 | Chen et al. | ..................... | 558/82 |
| 2002/0032279 A1* | 3/2002 | Hwang et al. | ................. | 525/107 |
| 2003/0073781 A1* | 4/2003 | Hwang et al. | ................. | 525/107 |
| 2003/0099839 A1* | 5/2003 | Hwang et al. | ................. | 428/413 |
| 2003/0120021 A1* | 6/2003 | Wang et al. | ..................... | 528/89 |
| 2004/0044168 A1* | 3/2004 | Hwang et al. | ................. | 528/89 |
| 2004/0077821 A1* | 4/2004 | Hwang et al. | ................. | 528/89 |
| 2004/0077825 A1* | 4/2004 | Hwang et al. | ................. | 528/398 |
| 2005/0004339 A1* | 1/2005 | Wang et al. | ..................... | 528/108 |
| 2007/0179217 A1* | 8/2007 | Hwang et al. | ................. | 523/458 |
| 2008/0064792 A1* | 3/2008 | Hwang et al. | ................. | 523/466 |
| 2009/0171120 A1* | 7/2009 | Lin et al. | ....................... | 568/12 |
| 2009/0258997 A1* | 10/2009 | Lin et al. | ....................... | 525/409 |
| 2010/0004426 A1* | 1/2010 | Lin et al. | ....................... | 528/399 |
| 2010/0016585 A1* | 1/2010 | Lin et al. | ....................... | 544/90 |
| 2010/0105939 A1* | 4/2010 | Chen et al. | ..................... | 558/82 |
| 2011/0172384 A1* | 7/2011 | Su et al. | ........................ | 528/89 |
| 2012/0116078 A1* | 5/2012 | Lin et al. | ....................... | 544/73 |
| 2013/0005938 A1* | 1/2013 | Lin et al. | ....................... | 528/168 |

FOREIGN PATENT DOCUMENTS

| | | | |
|---|---|---|---|
| JP | 61282388 A | * | 12/1986 |
| JP | 62036392 A | * | 2/1987 |
| TW | 575633 | | 2/2004 |

OTHER PUBLICATIONS

Derwent abstract JP 62036392A.*
Derwent abstract JP 61282388A.*

* cited by examiner

*Primary Examiner* — Jafar Parsa
*Assistant Examiner* — Amy C Bonaparte
(74) *Attorney, Agent, or Firm* — Edwards Wildman Palmer LLP; Peter F. Corless; Mark D. Russett

(57) ABSTRACT

The present invention provides a phosphorus compound of formula (I).

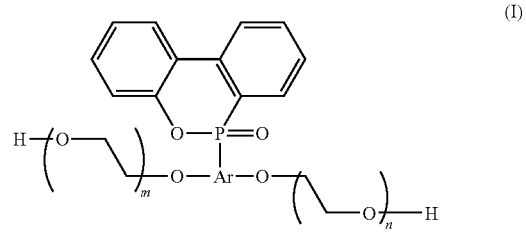

(I)

The phosphorus compound is prepared by reacting a compound of formula (II) with alkylene carbonate.

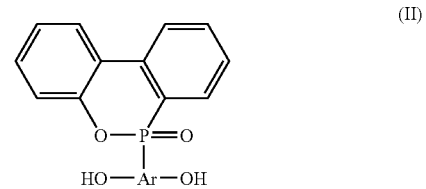

(II)

As compared with the conventional phosphorus compounds as flame-resistant additives, the phosphorus compound of the present invention has not only a high pyrolysis temperature but also excellent solubility in most of the organic solvents with high or low polarity, and is therefore a suitable flame-resistant additive for use in thermosetting or thermoplastic resins.

6 Claims, 4 Drawing Sheets

PHOSPHORUS COMPOUND AND METHOD FOR PREPARING THE SAME

BACKGROUND OF THE INVENTION

1. Field of the Invention

The present invention relates to phosphorus compounds and methods for preparing the same, and more particularly, to a phosphorous compound with high solubility and a method for preparing the same.

2. Description of Related Art

In order to meet the demand for thin circuits and high density, laminates need excellent electrical property, mechanical performance and particularly resistance to thermal processing. As to a common FR4 laminate, its glass transition temperature is approximately 130° C. after curing. During fabrication of printed circuit boards, laminates have cracking or a popcorn effect due to the processes of stripping and drilling over 200° C., or even welding processes over 270° C. Thus, there are developments on various types of laminate materials with high thermal stability and high glass transition temperatures. In addition, laminates have a further important property, flame resistance, which is advantageous to applications of laminates in some fields, for examples, transportation vehicles like planes, automobiles and public transportation vehicles. Hence, flame resistance of printed circuit boards is absolutely essential.

To increase flame resistance of laminate materials, certain substances having the property of insulating flame to reduce burning are used. As to laminates, halogen compounds, especially bromide-containing epoxy resins and curing agents, are used conventionally with flame retardants such as antimony trioxide to meet the requirement of flame resistance (e.g., UL 94V-0 level). Generally, an epoxy resin must have up to 17-21% bromide, and be used with antimony trioxide or other flame retardants to pass UL 94V-0. However, use of bromide-containing epoxy resins or antimony trioxide undoubtedly has adverse effects on human health, because antimony trioxide is reported as a carcinogenic compound. Further, during burning, bromide generates corrosive bromine radicals and hydrogen bromide, and high concentrations of aromatic compounds in bromide also generate highly toxic bromofurans and bromodioxins, thereby severely affecting human health and the environment.

Currently, the use of phosphorous compounds as the next generation of environmentally friendly flame retardant has been widely investigated and applied. For example, a flame-resistant epoxy resin composition formed from a phosphorus compound disclosed in Taiwanese Patent No. 575633 passes UL 94V-0, and does not release corrosive and highly toxic gases upon heating. However, phosphorus compounds, due to their own structures, are nearly insoluble in solvents commonly applied to epoxy resin compositions, and it is soluble only in solvents with higher polarity. Consequently, solvents with higher polarity are necessary if phosphorous compounds are to be used, thereby causing inconvenience in processing or application.

Accordingly, there still exists a need for a flame-resistant additive with high solubility and a high pyrolysis temperature, which is capable of being applied to thermosetting or thermoplastic resins.

SUMMARY OF THE INVENTION

It is an aspect of the present invention to provide a phosphorus compound with high solubility and a method for preparing the same.

It is another aspect of the present invention to provide a phosphorus compound with a high pyrolysis temperature and a method for preparing the same.

It is a further aspect of the present invention to provide a phosphorus compound that is capable of being used as a flame-resistant additive and a method for preparing the same.

In order to attain the above and other aspects, the present invention provides a phosphorous compound of formula (I):

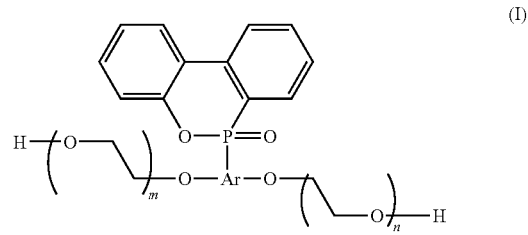

(I)

wherein Ar is a divalent group, which is one selected from the group consisting of naphthalene, anthracene, phenanthrene, anthrone, anthraquinone, biphenyl, diphenyl ether, diphenyl sulfide, diphenyl sulfone, diphenyl $(C_1\text{-}C_6)$alkyl and dinaphthyl $(C_1\text{-}C_6)$alkyl unsubstituted or with substituted alkyl having 1 to 6 carbon atoms, nitro group, halogen or phenyl; and m and n are independently an integer of 1 to 5.

The present invention also provides a method of preparing a phosphorus compound of formula (I). In the method of the present invention, a compound of formula (II) reacts with alkylene carbonate or alkylene oxide in a solvent, and then the solvent is removed under heating to obtain a phosphorus compound of formula (I).

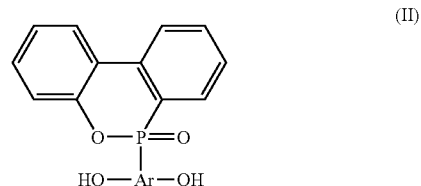

(II)

As compared with the conventional phosphorus compounds commonly as flame-resistant additives, the phosphorus compound of the present invention has not only a high pyrolysis temperature but also excellent solubility in most of the organic solvents with high or low polarity, and is therefore a suitable flame-resistant additive for use in thermosetting or thermoplastic resins.

DETAILED DESCRIPTION OF THE INVENTION

Figure 1:
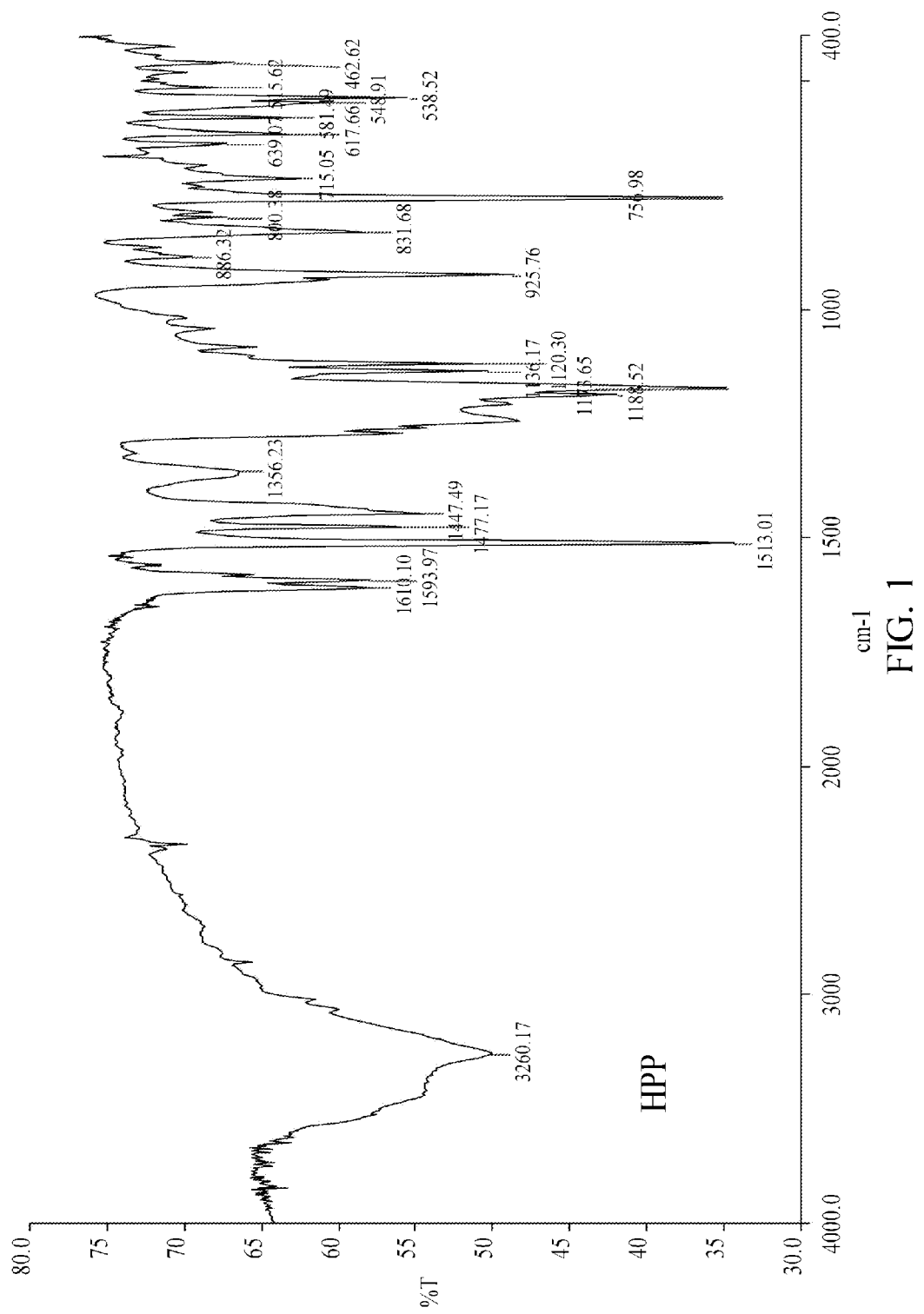
FIG. 1 is an FTIR analytical spectrum of a reactant HPP in Example 1.

The phosphorus compound of the present invention has a structure represented by formula (I):

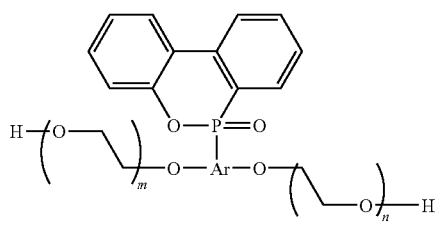

(I)

wherein Ar is a divalent group, which is one selected from the group consisting of naphthalene, anthracene, phenanthrene, anthrone, anthraguinone, biphenyl, diphenyl ether, diphenyl sulfide, diphenyl sulfone, diphenyl ($C_1$-$C_6$)alkyl, and dinaphthyl ($C_1$-$C_6$)alkyl unsubstituted or substituted with alkyl having 1 to 6 carbon atoms, nitro group, halogen or phenyl; and m and n are independently an integer of 1 to 5. Preferably, Ar is one selected from the group consisting of biphenyl and diphenyl ($C_1$-$C_6$)alkyl which are unsubstituted or substituted with alkyl having 1 to 6 carbon atoms, nitro group, halogen or phenyl; and m and n are independently an integer of 1 to 3. More preferably, Ar is a biphenyl divalent group; and m and n are independently an integer of 1 to 2.

In one embodiment, alkyl having 1 to 6 carbon atoms includes, but not limited to, methyl, ethyl, propyl, hexyl and cyclohexyl. Examples of halogen include fluoride, chloride, bromide and iodide. Examples of the divalent group, diphenyl ($C_1$-$C_6$)alkyl, include diphenylmethyl, diphenylethyl, diphenylpropyl, diphenylhexyl, and diphenylcyclohexyl. The divalent group, dinaphthyl ($C_1$-$C_6$)alkyl is one selected from the group consisting of dinaphthylmethyl, dinaphthylethyl, dinaphthylpropyl, dinaphthylhexyl and dinaphthylcyclohexyl.

In the present invention, (9,10-dihydro-9-oxa-10-phosphaphenanthrene-10-oxide-10-yl)-di(4-hydroxyphenyl)methane (HPP) reacts with alkylene carbonate or alkylene oxide in a solvent in the presence of a catalyst and under heating, and then the solvent is removed to obtain the phosphorus compound of formula (I). Examples of alkylene carbonate include, but not limited to, ethylene carbonate, propylene carbonate, fluoroethylene carbonate, chloroethylene carbonate, 5,5-diethyl-1,3-dioxolan-2-one and 5-methyl-5-propyl-1,3-dioxolan-2-one unsubstituted or substituted with alkyl having 1 to 6 carbon atoms, haloalkyl having 1 to 6 carbon atoms or halogen. In a preferred embodiment, ethylene carbonate is selected, and the reaction scheme is shown as follows.

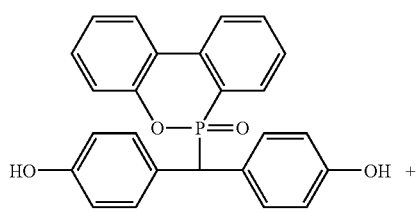

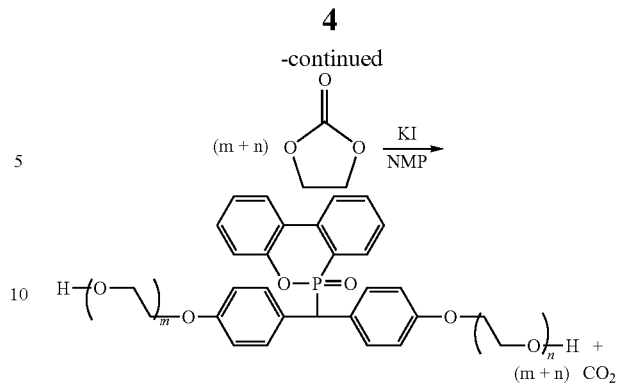

In another embodiment provided in the present invention, the method is performed by reacting (9,10-dihydro-9-oxa-10-phosphaphenanthrene-10-oxide-10-yl)-di(4-hydroxyphenyl)methane (HPP) with alkylene oxide such as ethylene oxide in a solvent in the presence of a catalyst and under heating, and then removing the solvent to obtain the phosphorus compound of formula (I). The reaction scheme is shown as follows.

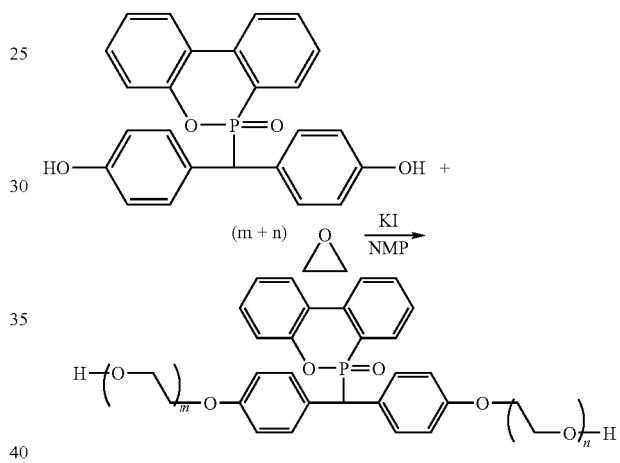

In a further embodiment provided in the present invention, the method is performed by reacting (9,10-dihydro-9-oxa-10-phosphaphenanthrene-10-oxide-10-yl)-di(4-hydroxyphenyl)methane (HPP) with an alcohol compound in a solvent containing an acid scavenger, and then removing the solvent to obtain the phosphorus compound of formula (I). The reaction scheme is shown as follows.

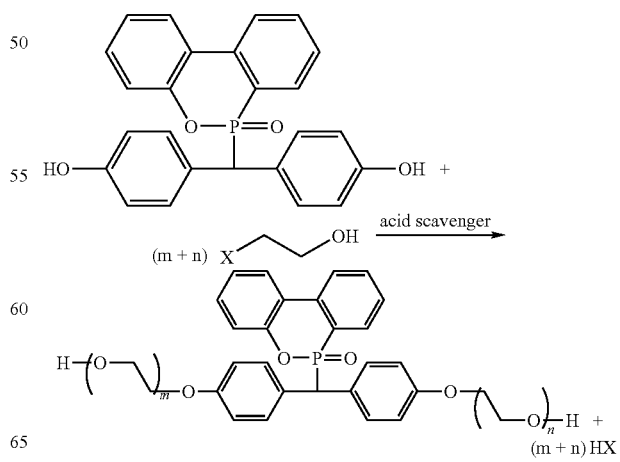

wherein X represents halogen.

In the method of the present invention, a reaction is performed at an increased temperature, such as in a range from 100° C. to 210° C., preferably in a range from 140° C. to 180° C., and more preferably in a range from 160° C. to 180° C. There is no particular limitation to the solvent used in the method, as along as the solvent can dissolve reactants and is readily removable. A preferred solvent is N-methylpyrrolidone.

The following examples are used to further illustrate the features, instead of intending to limit scope, of the present invention.

EXAMPLES

Example 1

414.4 g of (9,10-dihydro-9-oxa-10-phosphaphenanthrene-10-oxide-10-yl)-di(4-hydroxyphenyl)methane (HPP), 176.1 g of ethylene carbonate (EC), 0.6 g of KI and 1000 g of N-methylpyrrolidone were charged into a reactor, and then the mixture was heated under stirring to 150° C. to perform the reaction for 8 hours until carbon dioxide was no longer generated in the reactor. After the reaction finished, the solvent was removed by drying to obtain 468 g of product (HPPEC).

Figure 2:
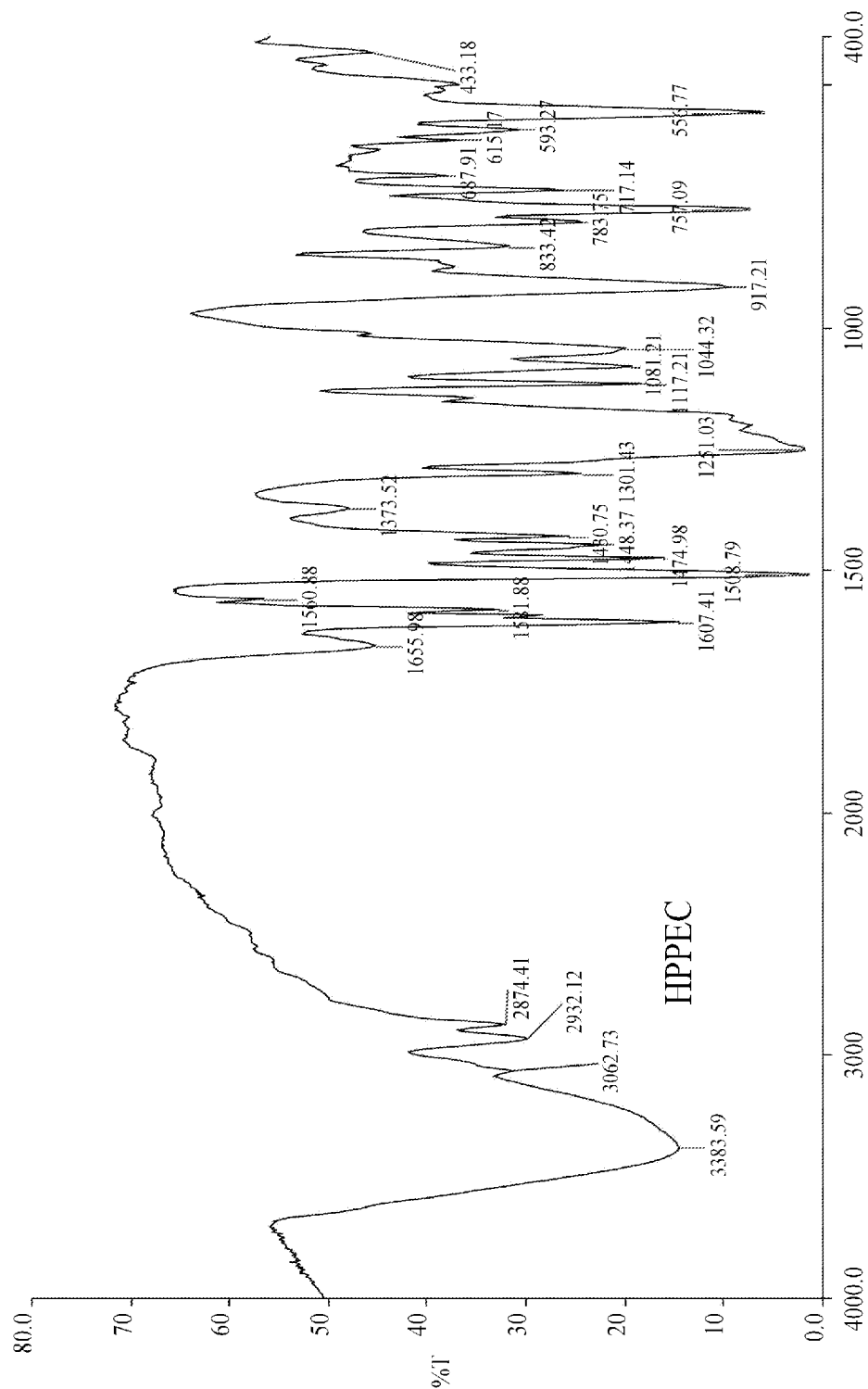
FIG. 2 is an FTIR analytical spectrum of a product HPPEC in Example 1.
Figure 3:
FIG. 3 is an NMR analytical spectrum of a product HPPEC in Example 1.

Elemental composition of the product analyzed by ESCA was C: 68.5%, H: 5.2%, O: 20.33% and P: 5.97% (when m+n=2, the theoretical composition was C: 69.32%, H: 5.42%, O: 19.10% and P: 6.16%). FIG. 1 shows an FTIR analytical spectrum of the reactant HPP, and FIG. 2 shows an FTIR analytical spectrum of the product HPPEC. As shown in FIG. 2, an absorption peak at 2,932 cm$^{-1}$ indicates that —CH$_2$— was attached on HPPEC, whereas an absorption peak at 1,251 cm$^{-1}$ indicates that the hydroxyl group on phenol was converted to an ether group. FIG. 3 shows an NMR spectrum of the product HPPEC. The softening point of resins was 95° C.

Example 2

Figure 4:
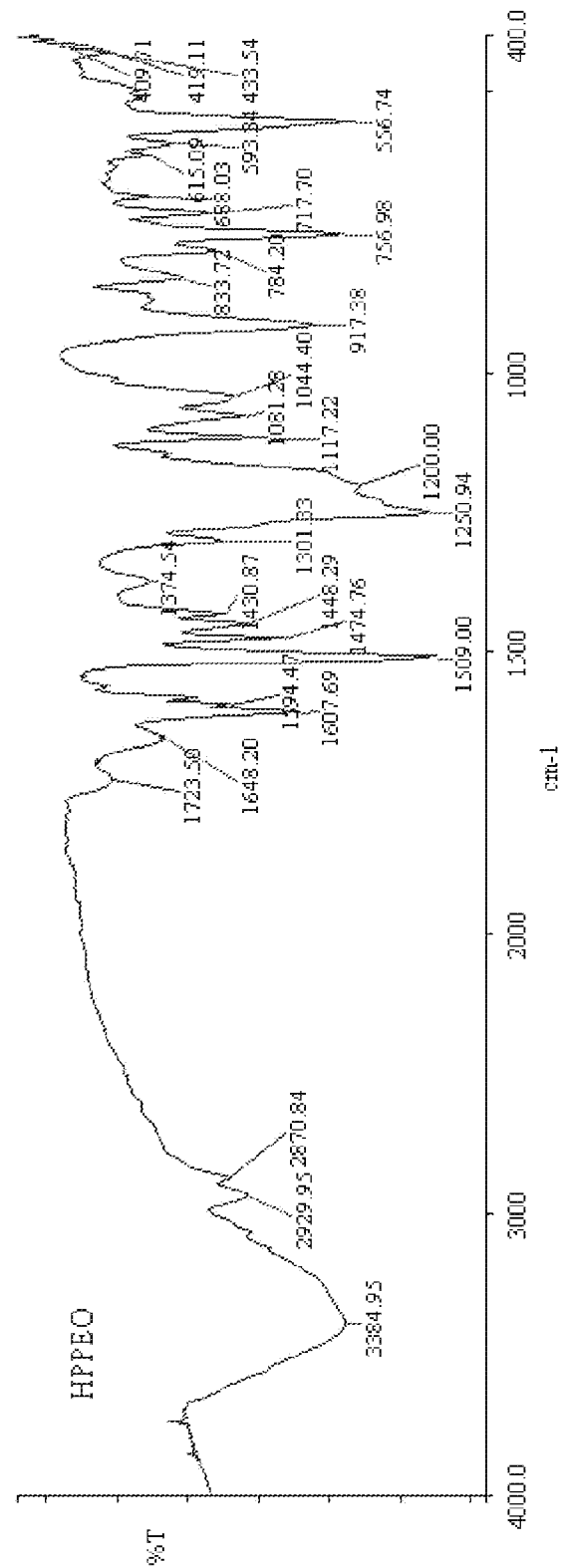
FIG. 4 is an FTIR analytical spectrum of a product HPPEC in Example 2.

207.2 g of (9,10-dihydro-9-oxa-10-phosphaphenanthrene-10-oxide-10-yl)-di(4-hydroxyphenyl)methane, 45 g of ethylene oxide, 0.3 g of KI and 500 g of N-methylpyrrolidone were charged into a reactor, and then the mixture was heated to 150° C. under stirring to perform the reaction for 8 hours until carbon dioxide was no longer generated in the reactor. After the reaction finished, the solvent was removed by drying and 230 g of product (HPPEO) was obtained. FIG. 4 shows an FTIR analytical spectrum of the product HPPEO. As shown in FIG. 4, an absorption peak at 2,930 cm$^{-1}$ indicates that —CH$_2$— was attached on HPPEO, whereas an absorption peak at 1,251 cm$^{-1}$ indicates that the hydroxyl group of phenol was converted to an ether group. The softening point of resins was 87° C.

Test Example 1

According to Table 1, 1 g of flame-resistant additive (HPP) and 1 g of the product (HPPEC) in Example 1 were dissolved in 20 g of solvent respectively, and the results are illustrated in Table 1.

TABLE 1

| Solvent | HPP | HPPEC |
|---|---|---|
| Toluene | X | X |
| Acetone (ACT) | X | ◇ |
| Methyl ethyl ketone(MEK) | X | ○ |
| Methanol | X | ○ |
| Ethanol | X | ○ |
| N-Methylpyrrolidone (NMP) | ○ | ◇ |
| Dimethylformamide (DMF) | ○ | ◇ |

X: insoluble
◇: readily soluble
○: soluble

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A phosphorus compound of formula (I):

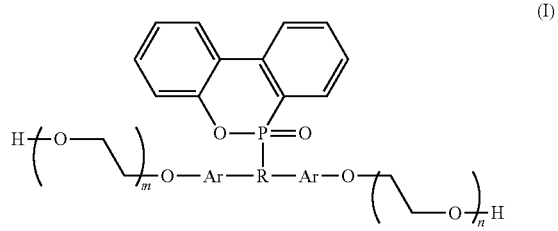

wherein R is a trivalent alkane group having 1 to 6 carbon atoms, and Ar is phenylene or naphthalene, and m and n are independently an integer of 1 to 5.

2. The compound of claim 1, wherein the trivalent alkane group is selected from the group consisting of methanetriyl, ethanetriyl, propanetriyl, hexanetriyl and cyclohexanetriyl.

3. A method for preparing the phosphorus compound having a structure represented by formula (I),

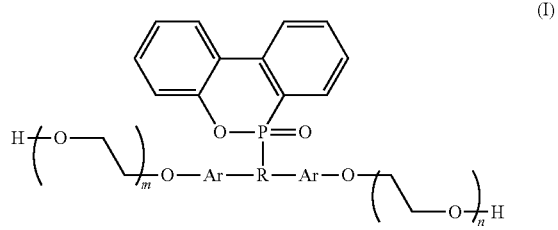

wherein R is a trivalent alkane group having 1 to 6 carbon atoms, and Ar is phenylene or naphthalene, and m and n are independently an integer of 1 to 5;

the method comprising the steps of:

reacting a compound of formula (II) with alkylene carbonate or alkylene oxide in a solvent under heating,

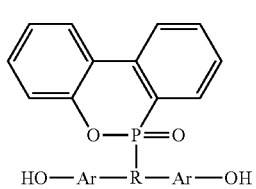
(II)

drying to remove the solvent and recover a product.

4. The method of claim 3, wherein the alkylene carbonate is unsubstituted or substituted with alkyl having 1 to 6 carbon atoms, haloalkyl having 1 to 6 carbon atoms or halogen.

5. The method of claim 3, wherein the alkylene carbonate is selected from the group consisting of ethylene carbonate, propylene carbonate, fluoroethylene carbonate, chloroethylene carbonate, 5,5-diethyl-1,3-dioxolan-2-one and 5-methyl-5-propyl-1,3-dioxolan-2-one.

6. The method of claim 3, wherein the alkylene oxide is ethylene oxide.

* * * * *